US009708238B2

(12) United States Patent
Decampo et al.

(10) Patent No.: US 9,708,238 B2
(45) Date of Patent: Jul. 18, 2017

(54) CYCLOALKANE OXIDATION CATALYSTS AND METHOD TO PRODUCE ALCOHOLS AND KETONES

(75) Inventors: Floryan Decampo, Pittsburgh, PA (US); Wenjuan Zhou, Shanghai (CN); Peng Wu, Shanghai (CN); Kai Xue, Shanghai (CN); Yueming Liu, Shanghai (CN); Mingyuan He, Shanghai (CN)

(73) Assignees: Rhodia Operations, Paris (FR); East China Normal University, Shanghai (CN); Ecole Normale Superieure De Lyon, Lyons (FR)

( * ) Notice: Subject to any disclaimer, the term of this patent is extended or adjusted under 35 U.S.C. 154(b) by 188 days.

(21) Appl. No.: 14/416,977

(22) PCT Filed: Jul. 26, 2012

(86) PCT No.: PCT/CN2012/079172
§ 371 (c)(1),
(2), (4) Date: Jan. 23, 2015

(87) PCT Pub. No.: WO2014/015491
PCT Pub. Date: Jan. 30, 2014

(65) Prior Publication Data
US 2015/0175514 A1 Jun. 25, 2015

(51) Int. Cl.
*C07C 49/385* (2006.01)
*C07C 35/02* (2006.01)
*C07C 45/28* (2006.01)
*C07C 29/48* (2006.01)

(52) U.S. Cl.
CPC .......... *C07C 49/385* (2013.01); *C07C 29/48* (2013.01); *C07C 35/02* (2013.01); *C07C 45/28* (2013.01); *C07C 2101/14* (2013.01)

(58) Field of Classification Search
CPC ....... C07C 49/385; C07C 35/02; C07C 45/28; C07C 29/48; C07C 2101/14
See application file for complete search history.

(56) References Cited

U.S. PATENT DOCUMENTS

| 2003/0040649 | A1 | 2/2003 | Oguchi et al. | |
| 2004/0034258 | A1* | 2/2004 | Oguchi | B01J 29/89 568/959 |
| 2006/0041172 | A1* | 2/2006 | Pirutko | C07C 45/33 568/338 |
| 2011/0237810 | A1* | 9/2011 | Kawabata | B01J 29/89 549/531 |

FOREIGN PATENT DOCUMENTS

| CN | 101733164 A | 6/2010 |
| CN | 102079695 A | 6/2011 |
| WO | WO 9408932 A1 | 4/1994 |
| WO | WO 0228774 A2 | 4/2002 |
| WO | WO 2004071998 A2 | 8/2004 |
| WO | WO 2007005411 A1 | 1/2007 |

OTHER PUBLICATIONS

Wu, Peng, et al—"Unique *trans*-Selectivity of Ti-MWW in Epoxidation of *cis/trans*-Alkenes with Hydrogen Peroxide", 2002, J. Phys. Chem. B, vol. 106, pp. 748-753; 6 pgs.

Wu, Peng, et al—"A novel titanosilicate with MWW structure III. Highly efficient and selective production of glycidol through expoxidation of allyl alcohol with $H_2O_2$", 2003, Journal of Catalysis, Science Direct, Academic Press, Elsevier, pp. 317-326; 10 pgs.

* cited by examiner

*Primary Examiner* — Peter F Godenschwager
*Assistant Examiner* — Andrew J Oyer
(74) *Attorney, Agent, or Firm* — Osha Liang LLP

(57) ABSTRACT

Disclosed is a method of oxidizing a cycloalkane to form a product mixture containing a corresponding alcohol and ketone, said method comprising contacting a cycloalkane with a hydroperoxide in the presence of a catalytic effective amount of a crystalline MWW-type titanosilicate catalyst. Hydroperoxides may notably be tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, and ethylnaphthalene hydroperoxide.

9 Claims, No Drawings

CYCLOALKANE OXIDATION CATALYSTS AND METHOD TO PRODUCE ALCOHOLS AND KETONES

This application is a U.S. national stage entry under 35 U.S.C. §371 of International Application No. PCT/CN2012/079172, filed Jul. 26, 2012. The entire content of this application is hereby incorporated herein.

The present invention concerns a method of oxidizing a cycloalkane to form a product mixture containing a corresponding alcohol and ketone, said method comprising contacting a cycloalkane with a hydroperoxide in the presence of a catalytic effective amount of a crystalline MWW-type titanosilicate catalyst. Hydroperoxides may notably be tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin, isobutylbenzene hydroperoxide, and ethylnaphthalene hydroperoxide.

PRIOR ART

Several different processes have been used for the oxidation of cyclohexane into a product mixture containing cyclohexanone and cyclohexanol. Such product mixture is commonly referred to as a KA (ketone/alcohol) mixture. The KA mixture can be readily oxidized to produce adipic acid, which is an important reactant in processes for preparing certain condensation polymers, notably polyamides. Given the large quantities of adipic acid consumed in these and other processes, there is a need for cost-effective processes for producing adipic acid and its precursors.

Heterogeneous catalysts processes have the advantage of easy separation and have been widely reported to catalyze the oxidation of cyclohexane. Many heterogeneous catalysts are based on mainly zeolite-like support incorporated or implemented transition metals or noble metals.

WO1994008032 reports a metal-incorporated molecular sieve containing aluminum, silicon and/or phosphorus oxides and applied them on the decomposition of cyclohexyl hydroperoxide. The lattice metal described is selected from the groups V B (W, etc.), VI B (Cr, etc.) and VII B (Co, etc.) of the Elemental Periodic system.

WO2007005411 discloses the oxidation of cyclohexane or catalytic decomposition of cycloalhexyl hydroperoxide using gold supported porous crystalline silicate containing less than about 2 wt. % aluminum or a crystalline phosphate. The crystalline silicate has a structure of BEA, FAU, MFI, MEL, MOR, MTW, MTT, MCM-22, MCM-41, MCM-48, NU-1. The crystalline phosphate has a structure of AFI, AEL, AFO, AFR, AFS, AFT, AFY, ATN, ATO, ATS, ATT, ATV, AWW. The crystalline silicate support is dealuminated zeolite having a structure selected from the group of AFI, AEL, AFO, AFR, AFS, AFT, AFY, ATN, ATO, ATS, ATT, ATV, AWW.

WO2004071998 describes a heterogeneous catalyst for so-call directly oxidation of cyclohexane. The catalyst is described of gold supported on a crystalline zeolite-like support which optionally contains one or more heteroatoms from the group of the element of Periods 2, 3, 4 and 5.

There remains a need of heterogeneous catalyst with high oxidation ability to get high conversion of cyclohexane and high selectivity to KA oil in relatively low cycloalkyl hydroperoxide concentration with low cost of catalyst preparation.

INVENTION

It appears now that it's perfectly possible to produce a mixture of alcohol and ketone from a cycloalkane with a high oxidation ability, high selectivity to KA oil with a good compromise of conversion and yield. Such results can be obtained with the use of a catalytic effective amount of a crystalline MWW-type titanosilicate catalyst.

The present invention then concerns a method of oxidizing a cycloalkane to form a product mixture containing a corresponding alcohol and ketone, said method comprising contacting a cycloalkane with a hydroperoxide in the presence of a catalytic effective amount of a crystalline MWW-type titanosilicate catalyst.

Cycloalkane

Cycloalkane may refer to saturated cyclic hydrocarbons having from 3 to about 10 carbon atoms, more usually from about 5 to about 8 carbon atoms. Non-limiting examples of cycloalkanes include cyclopentane, cyclohexane, cycloheptane, and cyclooctane.

Hydroperoxide

Specific examples of the hydroperoxide compounds which are usable in the present may be represented by the formula (I)

$$R-O-O-H \qquad (I)$$

wherein R may be a hydrocarbon group comprising 3 to 15 carbon atoms, mainly alkyl or aryl groups.

Hydroperoxides are preferably chosen in the group consisting of: tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e., tetrahydronaphtalene) hydroperoxide, isobutylbenzene hydroperoxide, and ethylnaphthalene hydroperoxide.

More preferably hydroperoxides are alkyl hydroperoxides such as tert-butyl hydroperoxide or cyclohexyl hydroperoxide.

These hydroperoxides may also be used in combination of two or more species thereof.

The hydroperoxides concerned with the invention may be generated in situ, notably by reaction of a cycloalkane with oxygen or an oxygen generator, or added to the reaction medium, notably at the start or during the reaction.

In an embodiment of the present invention, the reaction medium comprises a cycloalkane and 2 to 40 wt. % of hydroperoxides according to the total weight of the reaction, more preferably 5 to 20 wt. % of hydroperoxides.

Crystalline MWW-Type Titanosilicate Catalyst

Crystalline MWW-type titanosilicate catalyst of the present invention is defined according to the International Zeolite Association (hereinafter, simply referred to as "IZA") who defines the zeolite in W. Meier, D. H. Meier, D. H. Olxon and Ch. Baerlocher, Atlas of Zeolite Structure Types, 4$^{th}$ Edition, Elsevier (1996) (hereinafter, simply referred to as "Atlas"). The MWW structure, which is one known structure of molecular sieves, is characterized in that it has a pore comprising a ring structure containing 10 oxygen atoms and has a super cage (0.7×0.7×1.8 nm). This structure has been approved by IZA after the publication of the above-mentioned Atlas.

Crystalline MWW-type titanosilicate catalysts are notably described in JP63-297210, U.S. Pat. No. 6,759,540 and Peng Wu et al. "Journal of Catalysis" 214 (2003) 317-326.

Catalyst of the present invention may have several possible shapes which are modified from the original Ti-MWW lamellar precursor, for example; MWW-type lamellar structure, fully and partially delaminated form, like MCM-56, or pore expanded structures (like MCM-36).

This catalyst may have a MWW structure and being represented by the following chemical composition formula:

$xTiO_2.(1-x)SiO_2$, wherein x is comprised between 0.0001 and 0.5, More preferably, the value of x is from 0.01 to 0.13.

The catalyst of the invention may eventually further comprises one or more heteroatoms from the group of the element of Periods IB, IVB, VB, VIB, VIIB, VIIIB and VA, for example, aluminum, boron, vanadium, chromium, gallium, iron, bismuth, copper, gold and silver. Metals could be within the framework or in the extra framework.

Generally, the gel has molar ratios of additives, as defined in terms of moles of MWW-templating agent, moles of $SiO_2$ and moles of $TiO_2$, which comprise the following molar ratios: $TiO_2:SiO_2=0.5$-$5:100$; and MWW-templating agent: $SiO_2=10$-$500:100$. The water:$SiO_2$ molar ratio is typically from about 500-10000:100 and, if used, the solvent:$SiO_2$ molar ratio may be in the range of 0-5000:100.

Catalyst of the present invention may be used in a range comprised between 1 to 10 wt. %, preferably between 1 and 7 wt %, in relation to the total weight of the reaction medium.

Parameters of the Reaction

In the practice of the invention, the catalysts can be contacted with a cycloalkane, such as cyclohexane, by formulation into a catalyst bed, which is arranged to provide intimate contact between the catalyst and reactants. Alternatively, catalysts can be slurried with reaction mixtures using techniques known in the art. The process of the invention is suitable for either batch or continuous cycloalkane oxidation. These processes can be performed under a wide variety of conditions, as will be apparent to persons of ordinary skill.

Suitable reaction temperatures for the process of the invention typically range from about 20 to about 200° C., preferably from about 50 to about 200° C., more preferably from about 70 to about 140° C.

Reaction pressures often range from about 0.1 MPa (1 bar) to about 20 MPa (200 bar), such values not being absolutely critical. Cycloalkane reactor residence time generally varies in inverse relation to reaction temperature, and typically is comprised between 30 and 1440 minutes. Pure oxygen, air, oxygen-enriched or oxygen-depleted air or, alternatively, oxygen diluted with an inert gas, can be used in the reaction medium.

A solvent may be eventually employed in the reaction medium. Preferably solvents are chosen in the group of a polar protic or aprotic solvent, preferably acetonitrile or acetic acid.

The crystalline MWW-type titanosilicate catalyst for providing an oxidized compound generally has a tendency such that the activity thereof is decreased each time it is used repeatedly, and the catalyst after the repeated use cannot exhibit its initial activity. In such a case, the recovered catalyst may be regenerated or reproduced. The recovered catalyst may be regenerated by a conventionally known method. More specifically, the catalyst may be regenerated so that it has an initial activity, for example, by calcining the catalyst in air.

At the end of the reaction, the compound of interest may be eventually purified by well known methods of the technical field, such as distillation.

The following examples are provided for illustrative purposes only and should not be regarded as limiting the invention.

EXPERIMENTAL PART

Example 1

Synthesis of Ti-MWW Zeolite

Ti-MWW was synthesized using two steps according to the report of Prof. Wu's group (Wu P., *J. Phys. Chem. B* 2002, 106, 748-753). First, Ti-containing MWW was synthesized from fume silica (Cab-o-sil M7D), tetrabutyl orthotitanate, boric acid, piperidine (PI) and distilled water. Secondly, the Ti-containing precursors were then refluxed with 2M $HNO_3$ aqueous solution to remove extraframework Ti species and a part of framework boron. The solid product was filtered, washed, dried, and finally calcined at 550° C. for 10 h.

Example 2

Comparison of the Catalytic Property of Ti-MWW with Other Catalysts for the Oxidation of Cyclohexane Transition metal-implemented zeolites have been used to catalyze the oxidation of cylcohexane using t-butyl hydroperoxide (TBHP) at 80° C. for 1.0 h with 0.10 g catalyst and 6.0 wt. % TBHP in cyclohexane. Results are mentioned in Table 1.

TABLE 1

| Trials | Catalyst | TBHP Conversion (%) | KA Selectivity (%) | KA Yield (%) |
|---|---|---|---|---|
| C1 | None | 0.7 | 98.0 | 0.7 |
| C2 | Beta | 92.4 | 5.25 | 4.86 |
| C3 | Si-Beta | 1.09 | 98 | 1.07 |
| C4 | Cu-Beta | 51.6 | 26.8 | 13.82 |
| C5 | Fe—Cr-Beta | 98.9 | 15.6 | 15.43 |
| C6 | Co-Beta | 66.2 | 15.6 | 10.33 |
| C7 | Cr-Beta | 97.9 | 23.4 | 22.91 |
| C8 | Fe-MCM-22 | 70.2 | 15.6 | 10.95 |
| C9 | Na—Fe-MCM-22 | 41.2 | 13.6 | 5.60 |
| C10 | Fe-Beta | 99.5 | 12.6 | 12.54 |
| C11 | TS-1 | 10.1 | 28.5 | 2.88 |
| C12 | Ti MCM-41 | 16.9 | 43.5 | 7.1 |
| 1 | Ti-MWW | 10.7 | 90.1 | 9.64 |

It appears then that without any catalysts, TBHP conversion and KA yield are less than 1%. Beta with $Al^{3+}$ zeolite showed high TBHP conversion (92.4%) but poor KA selectivity. Without any $Al^{3+}$, pure silica beta zeolite had barely TBHP conversion and KA selectivity. After incorporation with transition metals ($Cu^{2+}$, $Fe^{3+}$, $Cr^{3+}$, $Co^{2+}$) into zeolites, the selectivity to KA oil and KA yield all increased compared to without transition metals. While all these catalysts had the problem of leaching active sites after first run, the best results in conversion, selectivity and yield are only obtained with the Ti-MWW zeolite catalyst.

It also appears here that the catalytic activity of zeolites on the oxidation of cyclohexane using TBHP as oxidant is not directly correlated with the effective pore size. It is more related to the structure of molecular sieves itself and the coordination state of titanium in molecular sieves. Here Ti-MWW showed the best selectivity to KA oil (90.1%) and the highest yield of KA oil (9.64%). Due to the limit of pore size, the catalytic activity of Ti-MWW on oxidation of cyclohexane mainly occurred in the half cage on the surface of zeolite.

What is claimed is:

1. A method of oxidizing a cycloalkane to form a product mixture containing a corresponding alcohol and ketone, said method comprising contacting a cycloalkane with a hydroperoxide in the presence of a catalytically effective amount of a crystalline MWW-type titanosilicate catalyst.

2. A method according to claim 1, in which the hydroperoxide is chosen in the group consisting of: tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, and ethylnaphthalene hydroperoxide.

3. A method according to claim 1, in which the hydroperoxide is added to the cycloalkane at the start of the step of contacting.

4. A method according to claim 1, in which the hydroperoxide is generated in situ by reaction of a cycloalkane with oxygen or an oxygen generator.

5. A method according to claim 1, in which the MWW structure is represented by the following chemical composition formula:

$$x\text{TiO}_2 \cdot (1-x)\text{SiO}_2,$$

wherein x is between 0.0001 and 0.5.

6. A method according to claim 1, in which the catalyst further comprises one or more heteroatoms from the group consisting of the elements of Periods IB, IVB, VB, VIB, VIIB, VIIIB and VA.

7. A method according to claim 1, in which the contacting is at a temperature of between 20 and 200° C.

8. A method according to claim 1, in which pure oxygen, air, oxygen-enriched air, oxygen-depleted air, or oxygen diluted with an inert gas is used in a reaction medium.

9. A method according to claim 1, in which the catalyst is used in a range of between 1 and 10 wt. %, in relation to the total weight of the reaction medium.

* * * * *